(12) United States Patent
Samuelson et al.

(10) Patent No.: US 6,925,331 B2
(45) Date of Patent: Aug. 2, 2005

(54) EGM SIGNAL ACQUISITION AND PROCESSING SYSTEM

(75) Inventors: Kent E. Samuelson, Parker, CO (US); Michael T. Hemming, Parker, CO (US); Michael W. Heinks, New Brighton, MN (US); Ross O. Starkson, Minneapolis, MN (US); Lori Durose-Schrimpf, Lino Lakes, MN (US); John D. Wahlstrand, Shoreview, MN (US)

(73) Assignee: Medtronic, Ind., Minneapolis, MN (US)

(*) Notice: Subject to any disclaimer, the term of this patent is extended or adjusted under 35 U.S.C. 154(b) by 285 days.

(21) Appl. No.: 10/261,314

(22) Filed: Sep. 30, 2002

(65) Prior Publication Data

US 2004/0064059 A1 Apr. 1, 2004

(51) Int. Cl.[7] ............................................... A61N 1/365
(52) U.S. Cl. ........................................................ 607/32
(58) Field of Search ............................. 607/27, 30, 32, 607/59, 60; 600/509, 510, 522

(56) References Cited

U.S. PATENT DOCUMENTS

| | | |
|---|---|---|
| 4,211,235 A | 7/1980 | Keller, Jr. et al. |
| 4,357,943 A | 11/1982 | Thompson et al. |
| 4,374,382 A | 2/1983 | Markowitz ............. 340/870.01 |
| 4,476,868 A | 10/1984 | Thompson |
| 4,539,992 A | 9/1985 | Calfee et al. |
| 4,550,732 A | 11/1985 | Batty, Jr. et al. |
| 4,556,063 A | 12/1985 | Thompson et al. |
| 4,676,248 A | 6/1987 | Berntson |
| 4,751,589 A | 6/1988 | Kominami et al. |
| 5,052,388 A | 10/1991 | Sivula et al. |
| 5,127,404 A | 7/1992 | Wyborny et al. |
| 5,345,362 A | 9/1994 | Winkler |
| 5,694,943 A | 12/1997 | Brewer et al. ............... 128/702 |
| 5,732,708 A | 3/1998 | Nau et al. .................... 128/710 |
| 5,978,713 A * | 11/1999 | Prutchi et al. ................. 607/60 |
| 6,304,772 B1 | 10/2001 | Taha et al. ................... 600/510 |
| 2002/0026122 A1 | 2/2002 | Lee et al. .................... 600/523 |

* cited by examiner

Primary Examiner—George Manuel
(74) Attorney, Agent, or Firm—Girma Wolde-Michael

(57) ABSTRACT

A system and method for acquiring and processing an EGM signal during a pacing event, wherein a unique converter code is generated upon digitizing of the EGM signal and encrypted in the EGM signal to demarcate a transient event. The system further provides dynamic filtering of the EGM signal and subsequent detection of an intrinsic event signal during the pacing event, from which rhythm events may be diagnosed and classified.

7 Claims, 7 Drawing Sheets

EGM SIGNAL ACQUISITION AND PROCESSING SYSTEM

BACKGROUND OF THE INVENTION

1. Field of the Invention

This invention relates generally to implantable medical devices and, more particularly, to processing intracardiac electrocardiogram (EGM) signals acquired from implantable medical devices during a pacing event.

2. Description of the Related Art

Since the introduction of the first implantable pacemakers in the 1960s, there have been considerable advances in both the fields of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than earlier ones. Today's state-of-the-art implantable medical devices are capable of performing significantly more complex tasks. The therapeutic benefits of such devices have been well proven.

As the functional sophistication and complexity of implantable medical device systems have increased over the years, it has become increasingly useful to include a system for facilitating communication between one implanted device and another implanted or external device, for example, a programming console, monitoring system, or the like. Shortly after the introduction of the earliest pacemakers, it became apparent that it would be desirable for physicians to non-invasively obtain information regarding the operational status of the implanted device, and/or to exercise at least some control over the device, e.g., to turn the device on or off or adjust the pacing rate, after implant. As new, more advanced features have been incorporated into implantable devices, it has been increasingly useful to convey correspondingly more information to/from the device relating to the selection and control of those features.

In particular, some of the important information relating to implantable pacemaker therapies concerns EGM signals. The EGM is the cardiac signal detected through the pacing electrodes. The amplification and filtering of the EGM signals for intrinsic events is well understood and is similar to sense amplifier signal processing. However, when pacing is performed as part of the implantable pacemaker therapies, the energies involved in the pacing are relatively high (on the order of volts) and the pulse widths are relatively short (on the order of msecs). The after-potential inherent in the lead system and the filter transient response mask the intrinsic events in conventional systems.

Paced EGM waveforms have historically had no value for discrimination and diagnosis of intrinsic events that could occur in a paced interval. The energy from pacing coupled through the bandpass and amplification detection circuitry results in signal amplitudes that conventionally prevent observation of cardiac events throughout the paced interval. Typically, the channel requires several intervals without pacing to settle down to a baseline that allows intrinsic cardiac event detection.

One conventional method to minimize pacing effects is to set the low frequency high-pass pole to a value of 18 Hz. However, one of the disadvantages of this method is that low frequency P-waves, R-waves and T-waves are distorted through differentiation. Similarly, filtering at greater fixed frequencies typically also provides unacceptable results.

Another conventional method is to reduce the gain of large signal amplitudes while maintaining sufficient gain for low amplitude signals, enabling observation of intrinsic cardiac events. This automatic gain control (AGC) function allows the channel to settle down toward the baseline more quickly than a fixed gain stage by limiting the large excursions of the output from the baseline. Moreover, by limiting the excursions of the amplifier circuitry from exceeding the common mode range, circuit recovery time is virtually eliminated. If the automatic gain control (AGC) function is mathematically described, then for any output, the input may be recreated mathematically.

The present invention is directed to overcoming, or at least reducing the effects of, one or more of the problems set forth above.

BRIEF DESCRIPTION OF THE DRAWINGS

The invention may be understood by reference to the following description taken in conjunction with the accompanying drawings FIG. 1 schematically illustrates an implantable medical device (IMD) system according to the present invention.

Figure 1:
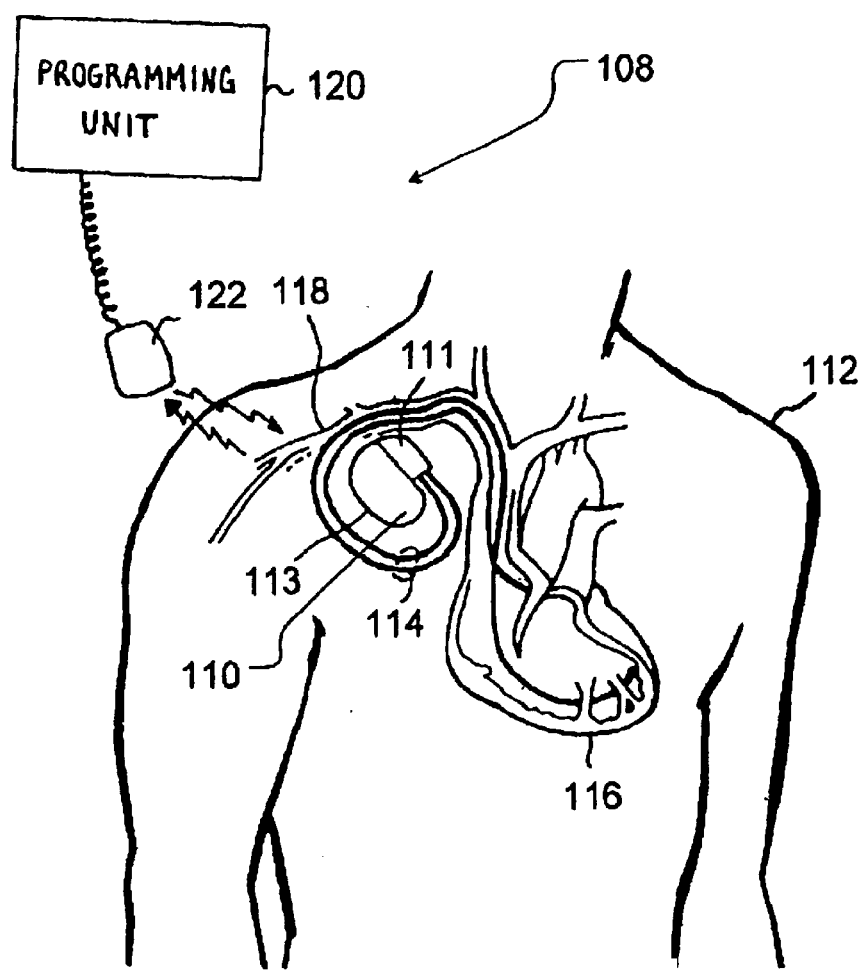

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of an apparatus and a method for operation of the apparatus according to the present invention are shown in FIGS. 1-8. FIG. 1 illustrates an implantable medical device (IMD) system 108, which includes, for example, an implantable pacemaker 110 that has been implanted in a patient 112. The pacemaker 110 is housed within a hermetically sealed, biologically inert outer canister or housing 113, which may itself be conductive so as to serve as an electrode in the pacemaker's pacing/sensing circuit. One or more pacemaker leads, collectively identified with reference numeral 114 in FIG. 1 are electrically coupled to the pacemaker 110 in a conventional manner and extend into the patient's heart 116 via a vein 118. Disposed generally near a distal end of the leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

Although the present invention is described herein in an embodiment that includes a pacemaker, it may be advantageously embodied in numerous other types of implantable medical device systems in which it is desirable to provide a communication link between two physically separated components and retrieve data stored therein.

FIG. 1 also depicts an external programming unit 120 for non-invasive communication with the implanted device 110 via conventional uplink and downlink communication channels, which are not described in greater detail herein so as to avoid unnecessarily obscuring the instant invention. Associated with the programming unit 120 is a programming head 122, in accordance with conventional medical device programming systems, for facilitating two-way communication between the pacemaker 110 and the programmer 120. In many known implantable device systems, the programming head 122, such as that depicted in FIG. 1, is positioned on the patient's body over the implant site of the device 110 (usually within about 2 to about 3 inches, or equivalently, about 5 to about 8 cm, of skin contact), such that one or more antennas within the head 122 can send radio frequency (RF) signals to, and receive radio frequency (RF) signals from, an antenna (not shown) disposed within the hermetic enclosure of the implanted device 110 or disposed within a connector block 111 of the device 110, in accordance with common practice in the art.

Figure 2:
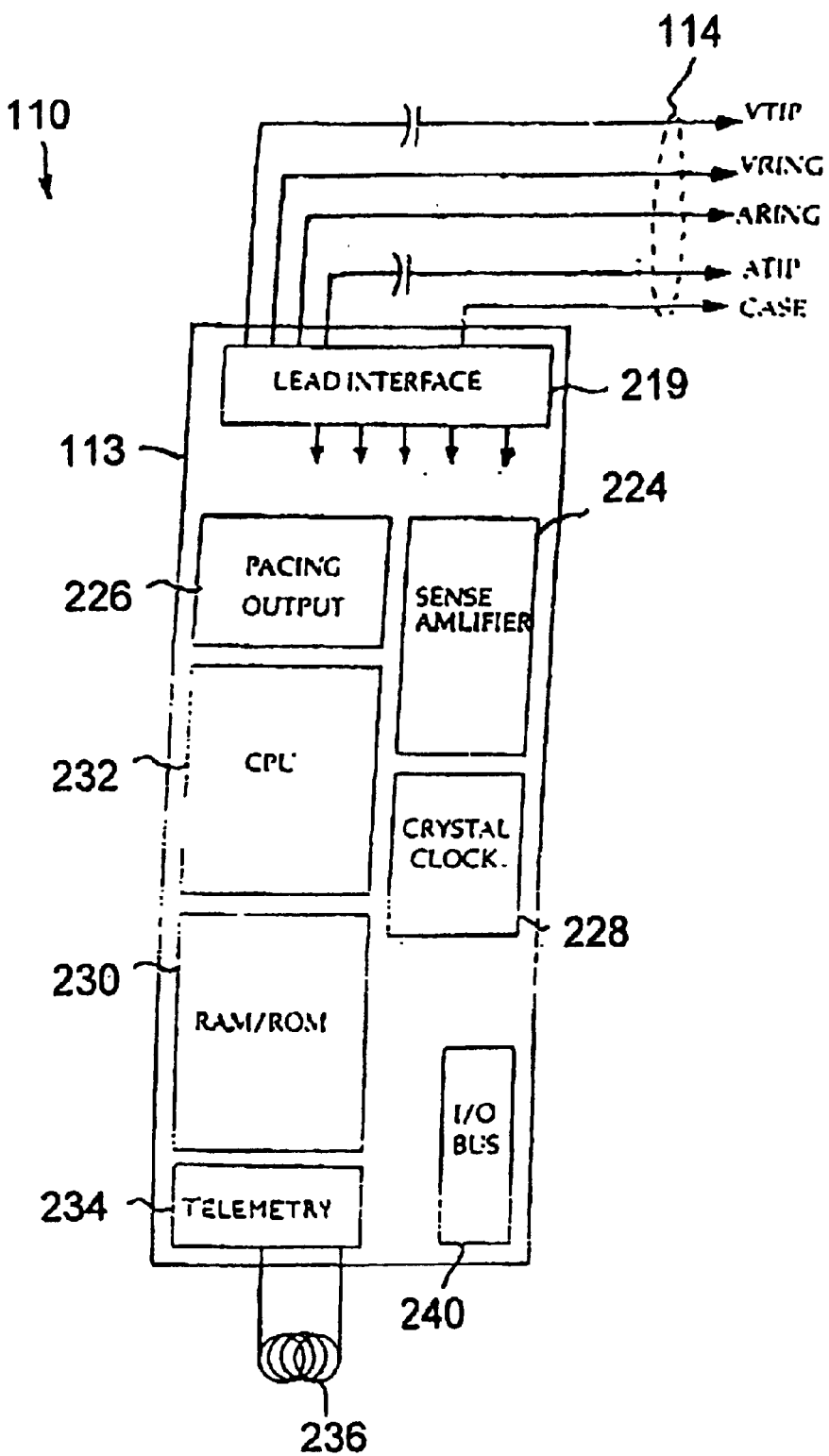
FIG. 2 schematically illustrates a general block diagram of electronic circuitry for the implantable medical device (IMD) system of FIG. 1.

FIG. 2 provides a general block diagram of electronic circuitry that makes up the pacemaker 110. The pacemaker 110 is a device capable of performing a variety of functions, such as delivering electrical stimulation therapy to the patient 112 in accordance with the presently disclosed embodiment of the invention. FIG. 2 shows that pacemaker 110 comprises circuitry for controlling the device's pacing and sensing functions. Aspects of the pacemaker circuitry may be of conventional design, in accordance; for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random-access memory and read-only memory (RAM/ROM) unit 230, and a pacing timing and control circuit in the form of a programmed central processing unit (CPU) 232, all of which are well-known in the art.

The pacemaker 110 also includes an internal telemetry communications circuit 234 coupled to an antenna 236 so that it is capable of communicating with the external programmer/control unit 120. Various telemetry systems for providing the uplink and downlink communication channels between the external programming unit 120 and the implanted pacemaker 110 have been shown in the art and may be employed herein without departing from the spirit and scope of the instant invention. Exemplary communication telemetry systems that may be utilized herein are disclosed, for example, in the following U.S. Patents: U.S. Pat. No. 4,539,992 to Calfee et al. entitled "Method and Apparatus for Communicating With Implanted Body Function Stimulator," U.S. Pat. No. 4,550,732 to Batty Jr. et al. entitled "System and Process for Enabling a Predefined Function Within An Implanted Device," U.S. Pat. No. 4,751,589 to Slocum et al. entitled "Biomedical Implant With High Speed, Low Power Two-Way Telemetry," U.S. Pat. No. 4,676,248 to Berntson entitled "Circuit for Controlling a Receiver in an Implanted Device," U.S. Pat. No. 5,127,404 to Wyborny et al. entitled "Telemetry Format for Implanted Medical Device," U.S. Pat. No. 4,211,235 to Keller, Jr. et al. entitled "Programmer for Implanted Device," the above-referenced Markowitz '382 patent and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, a conventional connector block assembly 111, shown in FIG. 1 but not shown in FIG. 2, facilitates the connections between the leads 114 and the various internal components of the pacemaker 110. Electrically, the coupling of the leads 114 and the internal electrical components of the pacemaker 110 may be facilitated by a lead interface circuit 219, which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuitry 226, in accordance with common practice, such that cardiac electrical signals may be conveyed to the sense amplifier circuitry 224, and such that stimulating pulses may be delivered to cardiac tissue, via the leads 114.

It will be appreciated that the signals received over the leads 114 by the sense amplifier circuitry 224 may be collected and stored in the RAM/ROM unit 230 by the CPU 232 acting under control of software also stored in the RAM/ROM unit 230. Additional data, such as the timing of signals delivered by the stimulating pulse output circuitry 226 may also be stored in the RAM/ROM unit 230. This stored data may be later retrieved and delivered to the programming unit 120 via the telemetry communications circuit 234.

As previously noted, the circuitry of the pacemaker 110 includes the central processing unit (CPU) 232 which may be an off-the-shelf programmable microprocessor or microcontroller, but in the presently illustrated embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of a program of instructions stored in the RAM/ROM unit 230. The crystal clock 228 in the presently illustrated embodiment is a crystal-controlled oscillator that provides a main timing clock signal. Again, the lines over which such clock signals are provided to the various components of the pacemaker 110 (e.g., the CPU 232) are omitted from FIG. 2 for the sake of clarity. It is believed that those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

Stimulating pulse output circuitry 226, which functions to generate cardiac stimuli under control of signals issued by the CPU 232, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 224, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pacemaker 110 in accordance with common practice in the art. In addition, these event-indicating signals, as discussed above, may be communicated, via the uplink communication channel, to the external programming unit 120 for storage and visual display to a physician or clinician.

Those of ordinary skill in the art will appreciate that the pacemaker 110 may include numerous other components and subsystems, for example, activity sensors and associated circuitry. The presence or absence of such additional components in the pacemaker 110, however, is not believed to be directly pertinent to the present invention.

Figure 3:
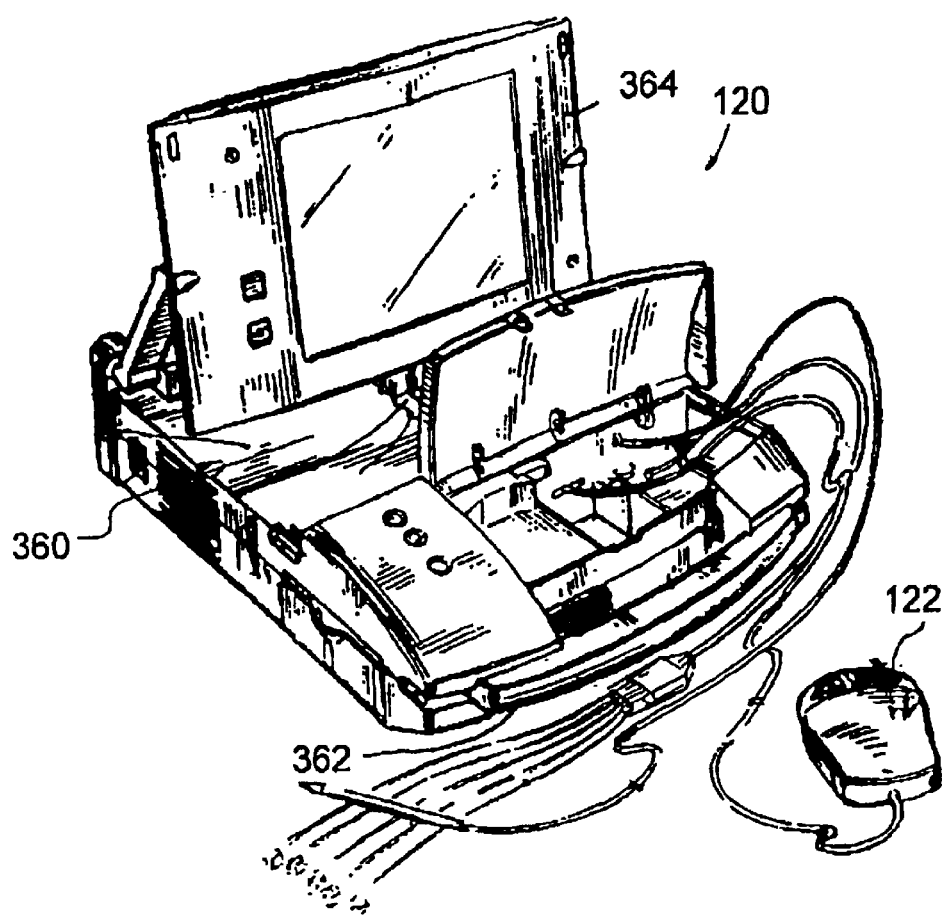
FIG. 3 schematically illustrates a perspective view of one embodiment of the programming unit for the implantable medical device (IMD) system of FIG. 1.

FIG. 3 shows a perspective view of one embodiment of the programming unit 120 in accordance with the presently disclosed embodiment of the invention. Internally, the programmer 120 includes a processing unit (not shown), which in accordance with the presently disclosed embodiment of the invention is a personal computer-type motherboard, for example, a computer motherboard including an Intel 80×86 microprocessor or the like and related circuitry such as digital memory.

Referring to FIG. 3, the programming unit 120 comprises an outer housing 360, which is preferably made of thermal plastic or another suitably rugged yet relatively lightweight material. A carrying handle, designated generally as 362 in FIG. 3, is integrally formed into the front of the housing 360. With the handle 362, the programming unit 120 can be carried like a briefcase.

An articulating display screen 364 is disposed on an upper surface of the housing 60. The display screen 364 folds down into a closed position (not shown) when the programming unit 120 is not in use, thereby reducing the size of the programming unit 120 and protecting the display surface of the display 364 during transportation and storage thereof.

A floppy disk drive is disposed within the housing 360 and is accessible via a disk insertion slot (not shown). A hard disk drive is also disposed within the housing 360, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 120 to adapt its mode of operation depending upon the type of implanted device to be programmed.

Accordingly, it may be desirable to have an expansion cartridge containing EPROMS or the like for storing program information to control the programming unit 120 to operate in a particular manner corresponding to a given type of implantable device.

In accordance with the presently illustrated embodiment of the invention, the programming unit 120 is equipped with an internal printer (not shown) so that a hard copy of a patient's electrocardiogram (ECG) or of graphics displayed on the programmer's display screen 364 can be generated. Several types of printers, such as the AR-100 printer available from General Scanning Co., are known and commercially available.

In the perspective view of FIG. 3, the programming unit 120 is shown with the articulating display screen 364 having been lifted up into one of a plurality of possible open positions such that the display area thereof is visible to a user situated in front of the programming unit 120. The articulating display screen 364 is preferably of the LCD or electro-luminescent type, characterized by being relatively thin as compared, for example, a cathode ray tube (CRT) or the like.

The display screen 364 is operatively coupled to computer circuitry disposed within the housing 360, and is adapted to provide a visual display of graphics and/or data under control of the internal computer.

One embodiment of the programming unit 120 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
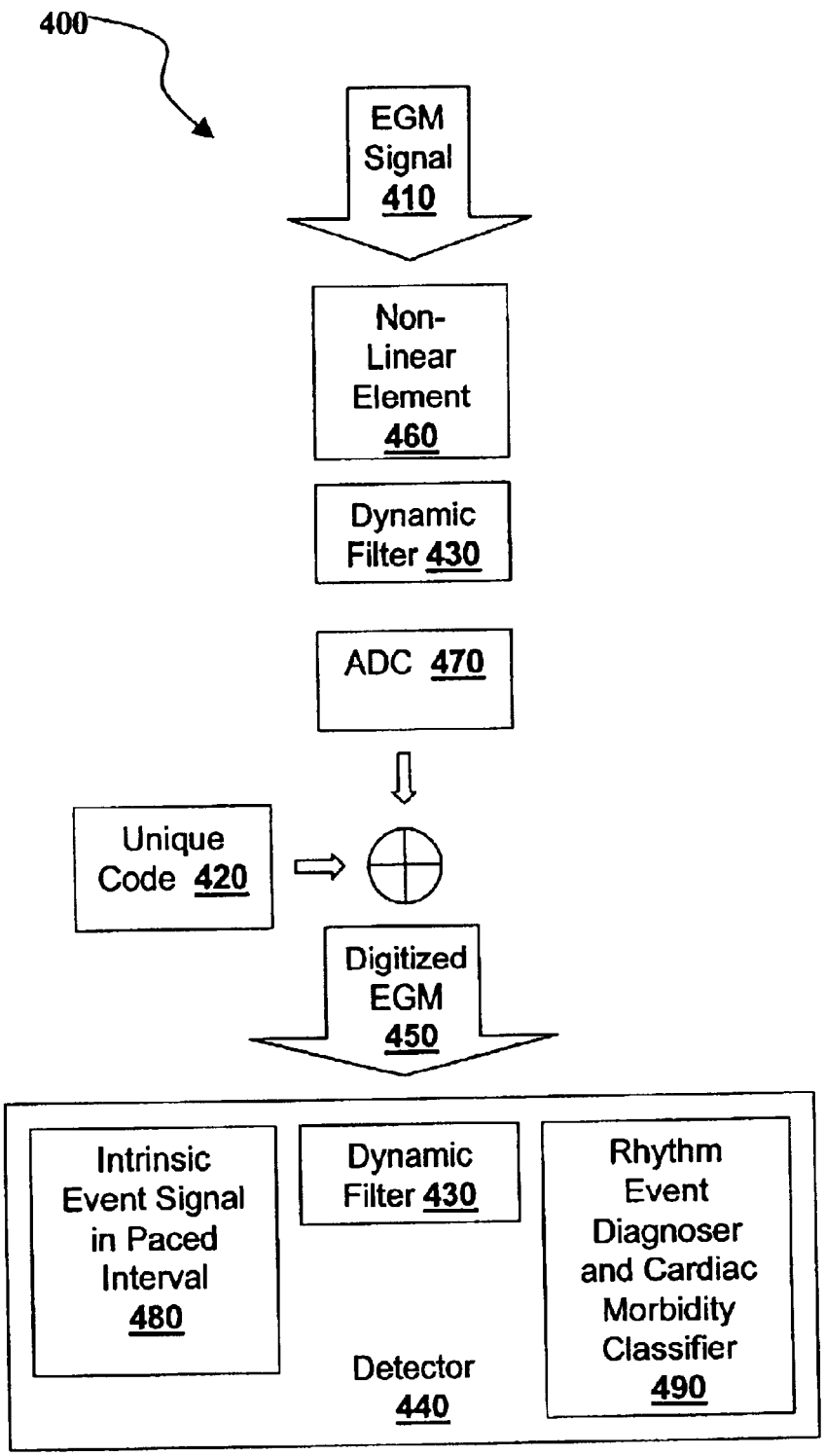
FIG. 4 schematically illustrates a general block diagram of an embodiment of an EGM signal acquisition and processing system according the present invention.

Turning to FIG. 4, a general block diagram illustrates an embodiment of an EGM signal acquisition and processing system 400 according the present invention. The system 400 includes an EGM signal 410 acquired via pacing electrodes, of leads 114 (FIGS. 1 and 2), during a pacing event, an analog-to-digital converter (ADC) 470, a unique code 420 encrypted in the EGM signal 410 to demarcate a transient event, and a bus 450 to carry a digitized EGM to a detector 440. The system 400 may further include a non-linear element 460 and a dynamic filter 430. The non-linear element 460, which may be a diode, may be used to limit a saturation of standard amplifier and filter stages caused by voltage excursions of large transients. The dynamic filter 430 is shown both prior to the ADC 470 and within the detector 440, since dynamic filtering may occur either before or after analog-to-digital conversion of the EGM signal 410. The detector 440 detects an intrinsic event signal in paced interval 480 and is capable of diagnosing rhythm events to classify cardiac co-morbidities during the paced interval, using a rhythm event diagnoser and cardiac co-morbidity classifier 490, for example. Note that the terms 'pacing event' and 'paced interval' are used interchangeably.

The dynamic filter 430 may be capable of processing the EGM signal 410 by performing the dynamic filtering either in the external programming unit 120 (using 3 fixed frequency circuits and switching between them, for example) and/or in the pacemaker 110 (using a variable resistor to modulate an RC circuit, for example). The pacemaker 110 may comprise an implantable anti-brady pacemaker and/or an implantable anti-tachy pacemaker. The dynamic filter 430 may be capable of processing the EGM signal 410 using a real-time algorithm.

The ADC 470 is capable of converting the EGM signal 410 to a numeric representation, the digitized EGM transferred by the bus 450 to detector 470. The unique code 420 encrypted in the EGM signal 410 may be generated by a first analog-to-digital conversion in the ADC 470 during a pacing event and may be used to demarcate the beginning of the paced event during signal processing. Furthermore, the unique code 420 may be used not only for real time processing, but also for delayed processing and/or recreation after data compression.

Within the detector 440, the digitized EGM, transferred from the bus 450, is numerically altered via an inverse automatic gain control function to obtain a numeric equivalent of the original input. The dynamic filter 430 may be capable of processing the EGM signal 410 by dynamically filtering the numeric equivalent of the original input using digital signal processing (DSP) techniques.

Figure 5:
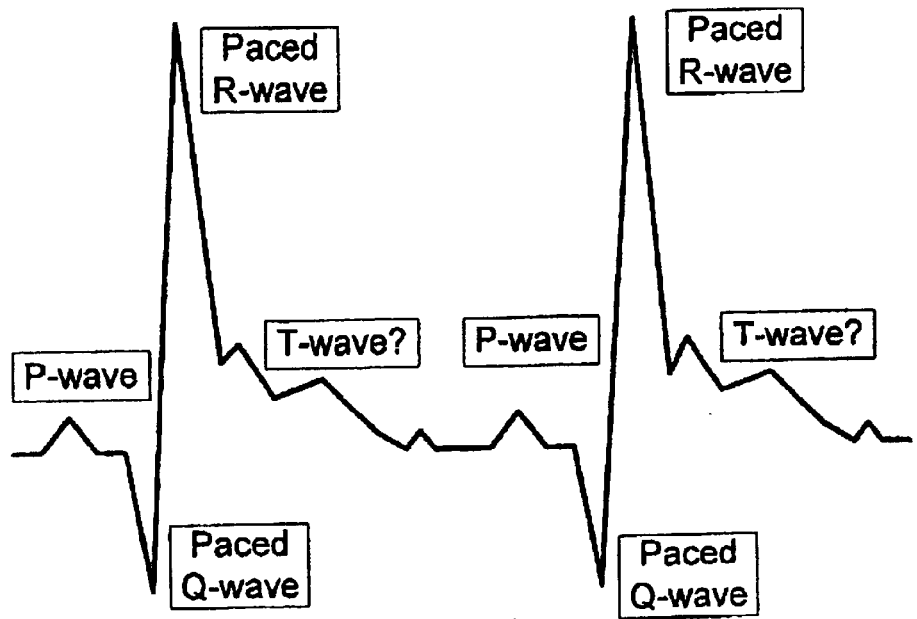
FIG. 5 schematically illustrates a P-wave followed by a paced Q-wave and a paced R-wave.
Figure 6:
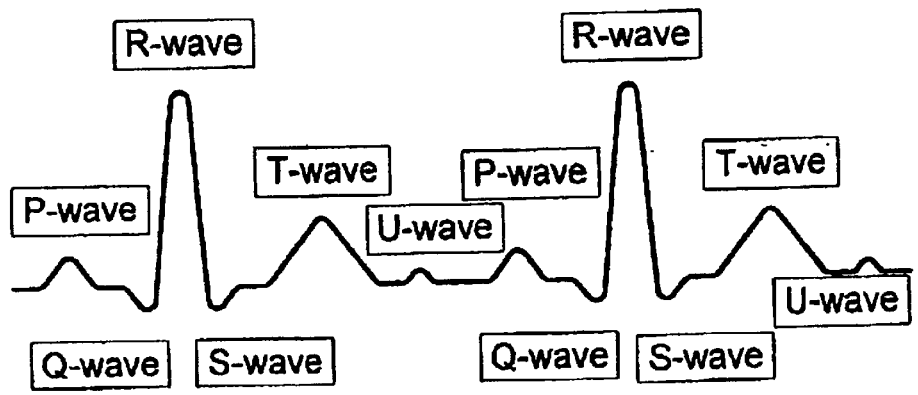
FIG. 6 schematically illustrates the paced signal as shown in FIG. 5, after having been processed by the system depicted in FIG. 4.

As shown in FIG. 5, a paced Q-wave and a paced R-wave follow a P-wave. Note that the paced R-wave signal may be about 1000 times the magnitude of an intrinsic (unpaced) R-wave signal, for example. Following the pacing, the T-wave may be obscured (as indicated by the designation "Possible T-wave" in FIG. 5). As shown in FIG. 6, when the paced signal as shown in FIG. 5 has been processed by the system 400, for example, using one of the methods described in more detail below in conjunction with FIGS. 7 and 8, the T-wave, and even an S-wave and a U-wave, may be detected following the pacing.

Figure 7:
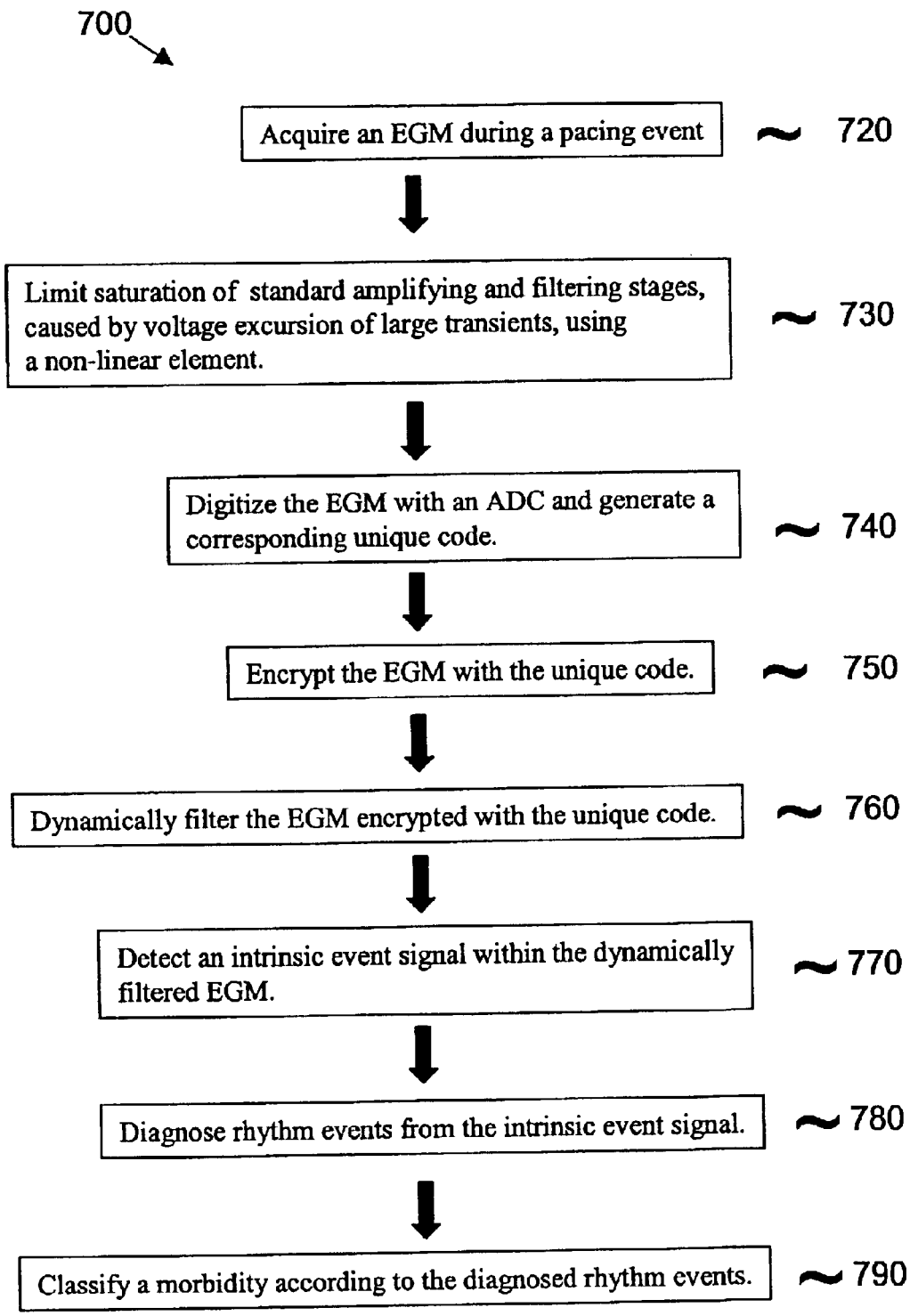
FIG. 7 schematically illustrates an embodiment of a method according the present invention.
Figure 8:
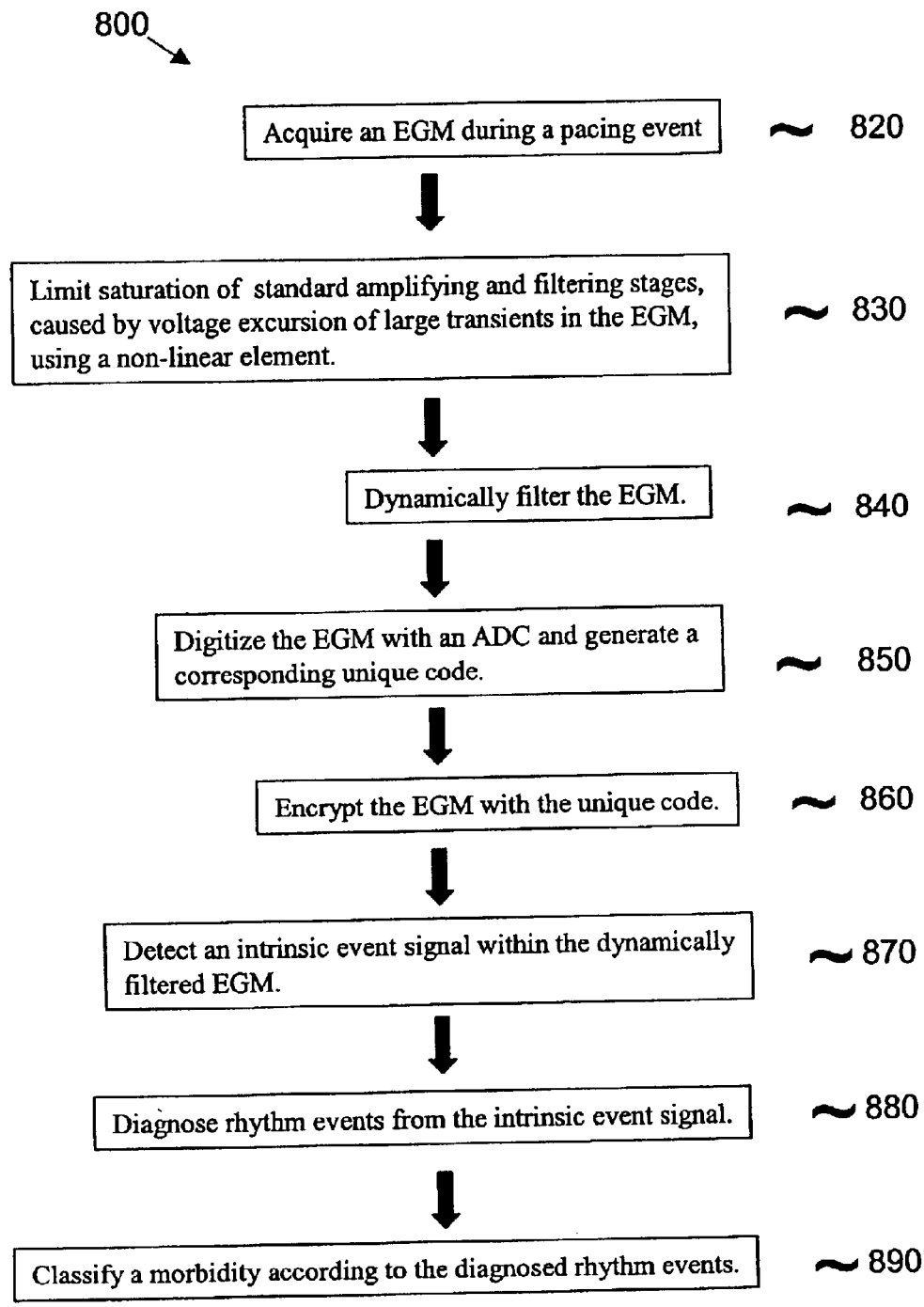
FIG. 8 schematically illustrates an alternative embodiment of a method according the present invention.

FIGS. 7 and 8 schematically illustrate particular embodiments of respective methods 700 and 800 practiced in accordance with the present invention, with reference to elements depicted in FIG. 4 and described herein above.

As shown in FIG. 7, method 700 begins, as set forth in a step 720, by acquiring the EGM signal 410 during a pacing event. In a step 730, the non-linear element 460 is used to limit saturation of standard amplifying and filtering stages caused by voltage excursions of large transients. According to the present invention, this is accomplished without additional blanking stages (other than a sense amp analog blanking stage). The non-linear element 460 may be a diode, for example. The EGM signal 410, in a step 740, is digitized using the ADC 470; in conjunction with digitization, the unique code 420 is generated. The EGM signal 410 is then encrypted with the unique code 420, in a step 750, to demarcate a transient event. For example, the unique code 420 may have been encrypted in the EGM signal 410 to demarcate the beginning of the pacing event. The method 700 proceeds by processing the EGM signal 410 with dynamic filtering, using the dynamic filter 430, as set forth in a step 760. According to the present invention, the dynamic filter 430 processes the EGM signal 410 by applying a high-pass pole, equivalent to about 15–40 Hz and preferably 18 Hz, at the beginning of the pacing event for about 150–300 milliseconds (msec), preferably for about 300 msec, then smoothly transitioning to a low-pass pole, equivalent to about 0.1–0.4 Hz and preferably 0.4 Hz, over about 100–300 msec, preferably 200 msec, and maintaining the low-pass pole until the next pacing event. Application of the high-pass pole at the beginning of the pacing event for about 150–300 msec enables passage of a higher frequency content cardiac R-wave and attenuates a portion of an artifact of the pacing event. The low-pass pole allows passage of a lower frequency content cardiac T-wave and allows subsequent intrinsic signals to be analyzed. In various illustrative embodiments, the EGM signal 410 may be processed with the dynamic filtering in either the receiver/programmer 120 (FIGS. 1 and 3) or within the pacemaker 110 (FIGS. 1 and 2).

Continuing to refer to method 700, the detector 440, in a step 770, detects an intrinsic event signal in paced interval 480 of EGM signal 410, which has been dynamically filtered. In steps 780 and 790 detector 440 uses the rhythm event diagnoser and cardiac co-morbidity classifier 490 to diagnose rhythm events from intrinsic event signal 480 and to classify a co-morbidity according to diagnosed rhythm events.

As shown in FIG. 8, method 800 begins, as set forth in a step 820, by acquiring the EGM signal 410 during a pacing event. In a step 830, the non-linear element 460 is used to limit saturation of standard amplifying and filtering stages caused by voltage excursions of large transients. According to the present invention, this is accomplished without additional blanking stages (other than a sense amp analog blanking stage). The non-linear element 460 may be a diode, for example. The method 800 proceeds by processing the EGM signal 410 with dynamic filtering (using the dynamic filter 430, for example), as set forth in a step 840, before digitizing and encrypting, whereas in method 700, described herein above, dynamic filtering follows digitizing and encrypting. Dynamic filter 430 processes EGM signal 410 in a manner similar to that described for step 760 of method 700. The EGM signal 410, in a step 850, is digitized using the ADC 470; in conjunction with digitization, the unique code 420 is generated. The EGM signal 410 is then encrypted with the unique code 420, in a step 860, to demarcate a transient event. For example, the unique code 420 may have been encrypted in the EGM signal 410 to demarcate the beginning of the pacing event. Steps 870–890 proceed in a fashion similar to that described for steps 770–790 of method 700 to diagnose and classify rhythm events.

In various illustrative embodiments, methods and devices according to the present invention may be used to allow continuous acquisition and processing of EGM signals through pacing events without loss of signal due to the pace or recharge energy. Same chamber QT interval signals and/or cross-chamber signals may be detected. Additionally, and/or alternatively, the QT interval may be measured after an intrinsic event and/or after a pace output. In various alternative illustrative embodiments, methods and devices according to the present invention may be applied to external electrical cardiac signals from LECG and/or other sources where a large transient occurs. The continuous EGM signal is also useful as a diagnostic for AF/AT and VF/VT events, and allowing detection immediately after a pacing therapy is a considerable improvement.

In other alternative illustrative embodiments, methods and devices according to the present invention may be applied to other sensor signals such as intracardiac pressure (dP/dt) where the filtered signal should be settled as soon as possible after a pace. In still other various alternative illustrative embodiments, methods and devices according to the present invention may allow detection of S-T segment elevation (an indicator of ischemia), for example, by shifting a high-pass pole to a low-pass pole, as described above.

Any of the above-disclosed embodiments of a method and a device according to the present invention enables an EGM signal to be acquired through a pacing event, a unique converter code having been encrypted in the EGM signal to demarcate a transient event. Additionally, any of the above-disclosed embodiments of a method and a device according to the present invention enables the EGM signal to be processed with dynamic filtering. Furthermore, any of the above-disclosed embodiments of a method and a device according to the present invention enables an intrinsic event signal in a paced interval to be detected using the dynamically filtered EGM signal and the unique converter code encrypted in the EGM signal. Any of the above-disclosed embodiments of a method and a device according to the present invention may also enable one or more of post-processing with dynamic filtering in the a receiver device with a simple real-time algorithm, using a unique code encrypted in the data to signal a transient event that could be used for real-time processing, delayed processing or recreation, using standard blanking, amplification and filtering stages, diagnosing rhythm events that afford classification of cardiac co-morbidities during paced events and using a non-linear stage or element to limit the voltage excursion due to large transients.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An EGM signal acquisition and processing system, comprising:

means for acquiring an EGM signal during a pacing event;

an analog-to-digital converter capable of converting the EGM signal from an analog a digital form;

means for generating an unique code;

a digital EGM signal encrypted with the unique code, the unique code demarcating a transient event;

a dynamic filter capable of dynamically filtering the EGM signal acquired during the pacing event; and a detector capable of detecting an intrinsic event signal within the digital EGM signal, wherein the means for dynamic filtering of the EGM signal includes;

means for applying a high-pass pole, the high-pass pole equivalent to about 15–40 Hz, at a beginning of the pacing event for about 150–300 msec;

means for smoothly transitioning from the high-pass pole to a low-pass pole, the low-pass pole equivalent to about 0.1–0.4 Hz, over about 100–300 msec; and means for maintaining the low-pass pole until a next pacing event.

2. The system of claim 1, wherein the detector includes means for diagnosing rhythm events from the intrinsic event signal and classifying the rhythm events according to cardiac co-morbidities.

3. An EGM signal acquisition and processing system, comprising:

means for acquiring an EGM signal during a pacing event;

an analog-to-digital converter capable of converting the EMG signal from an analog to a digital form;

means for generating an unique code;

a digital EGM signal encrypted with the unique code, the unique code demarcating a transient event;

a non-linear element capable of limiting saturation of standard amplifier and filter operations, the saturation caused by voltage excursions of large transient in the EGM signal acquired during a pacing event;

a dynamic filter capable of dynamically filtering the EGM signal; and a detector capable of detecting an intrinsic event signal within the digital EGM signal.

4. The system of claim 3, wherein the means for dynamic filtering of the EGM signal includes:

a means for applying a high-pass pole, the high-pass pole equivalent to about 15–40 Hz, at a beginning of the pacing event for about 150–300 msec;

a means for smoothly transitioning from the high-pass pole to a low-pass pole, the low-pass pole equivalent to about 0.1–0.4 Hz, over about 100–300 msec; and a means for maintaining the low-pass pole until a next pacing event.

5. The system of claim 3, wherein the detector includes means for diagnosing rhythm events from the intrinsic event signal and classifying the rhythm events according to cardiac co-morbidities.

6. A method for EGM signal acquisition and processing, comprising:

acquiring an EGM signal during a pacing event;

using a non-linear element to limit saturation of standard amplifying and filtering operations by voltage excursions caused by large transients in the EGM signal acquired during the pacing event;

dynamically filtering the EGM signal acquired during the pacing event;

digitizing the EGM signal acquired during the pacing event;

generating an unique code;

encrypting the digital EGM signal with the unique code; and detecting an intrinsic event signal within the dynamically filtered and digitized EGM signal.

7. The method according to claim 6, further comprising:

diagnosing rhythm events from the intrinsic event signal; and classifying a cardiac co-morbidity according to the diagnosed rhythm events.

\* \* \* \* \*

UNITED STATES PATENT AND TRADEMARK OFFICE
CERTIFICATE OF CORRECTION

| | | |
|---|---|---|
| PATENT NO. | : 6,925,331 B2 | Page 1 of 1 |
| APPLICATION NO. | : 10/261314 | |
| DATED | : August 2, 2005 | |
| INVENTOR(S) | : Samuelson et al. | |

It is certified that error appears in the above-identified patent and that said Letters Patent is hereby corrected as shown below:

Column 10, line 35, please delete "EMG" and insert --EGM--

Signed and Sealed this

Fifteenth Day of May, 2007

JON W. DUDAS
*Director of the United States Patent and Trademark Office*